(12) United States Patent
Day et al.

(10) Patent No.: US 6,606,918 B2
(45) Date of Patent: Aug. 19, 2003

(54) MULTI-AXIAL STRAIN TESTING APPARATUS

(75) Inventors: Gary L. Day, Hudson, OH (US);
Michael Carroll, Akron, OH (US);
Neal G. Sehm, Akron, OH (US)

(73) Assignee: Hankock Tire Mfg. Co., LTD., Seoul (KR)

( * ) Notice: Subject to any disclaimer, the term of this patent is extended or adjusted under 35 U.S.C. 154(b) by 0 days.

(21) Appl. No.: 09/850,257

(22) Filed: May 7, 2001

(65) Prior Publication Data

US 2002/0189370 A1 Dec. 19, 2002

(51) Int. Cl.[7] ............... G01N 3/08; G01N 3/32; G01N 3/00; G01D 7/00
(52) U.S. Cl. ............... 73/862.042; 73/826; 73/831; 73/853; 73/806
(58) Field of Search ............... 73/862.042, 826, 73/831, 834, 838, 853, 816, 817, 806

(56) References Cited

U.S. PATENT DOCUMENTS

| | | | |
|---|---|---|---|
| 3,776,030 A | | 12/1973 | Strimel |
| 3,807,224 A | * | 4/1974 | Hassenboehler ............ 73/831 |
| 3,958,452 A | * | 5/1976 | Hassenboehler ............ 73/828 |
| 4,248,096 A | | 2/1981 | Marcum |
| 4,327,572 A | * | 5/1982 | Pitman et al. ............ 73/7 |
| 4,535,636 A | | 8/1985 | Blackburn et al. |
| 4,548,085 A | * | 10/1985 | Grundy ............ 73/862.042 |
| 4,574,642 A | | 3/1986 | Fleischman |
| 4,677,854 A | * | 7/1987 | Gabelli ............ 222/101 |
| 4,936,135 A | * | 6/1990 | Annis et al. ............ 73/7 |
| 5,712,431 A | * | 1/1998 | Vilendrer ............ 73/841 |

OTHER PUBLICATIONS

The Relationship Between Uniaxial and Equibiaxial Fatigue in Gum and Carbon Black Filled Vulcanizates, Rubbercon '77, B. J. Roberts and J. B. Benzies, pp. 1–12, 2.1–2.13, 1977.
Standard Test Method for Rubber Deterioration–Crack Growth, ASTM Designation: D 813–95, ASTM Committee D–11 on Rubber, pp. 138, 139, and 142, May 1995.
Standard Test Method for Rubber Property–Vapor Transmission of Volatile Liquids, ASTM Designatioin: D 814–95, ASTM Committee D–11 on Rubber, pp. 143, Jul. 1995.
Standard Test Method for Rubber Property–Extension Cycling Fatigue, ASTM Designation: D 4482–85 (Reapproved 1994), ASTM Committee D–11 on Rubber, pp. 652–657, Jun. 1985.

* cited by examiner

Primary Examiner—Edward Lefkowitz
Assistant Examiner—Lilybett Martir
(74) Attorney, Agent, or Firm—Hudak, Shunk & Farine Co., LPA

(57) ABSTRACT

A strain testing apparatus which places tensile forces on a sheet, a film, or the like samples in at least two axes and generally in a radial direction. The multi-axial strain testing apparatus comprises a clamping assembly having at least two clamping members, and a sample securing portion arranged in a substantially radial manner about a point. The multi-axial strain testing apparatus can advantageously be employed to test crack growth propagation and flex fatigue in rubber polymer and elastomer samples.

19 Claims, 4 Drawing Sheets

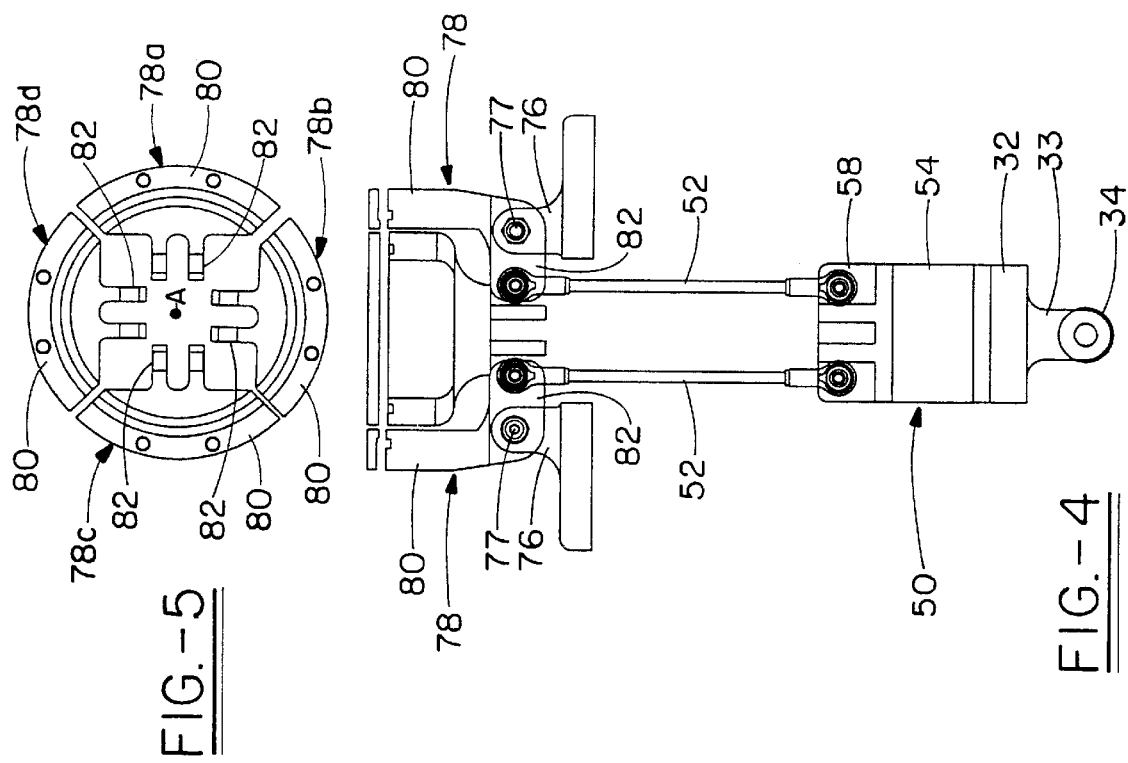
FIG.-5
FIG.-4
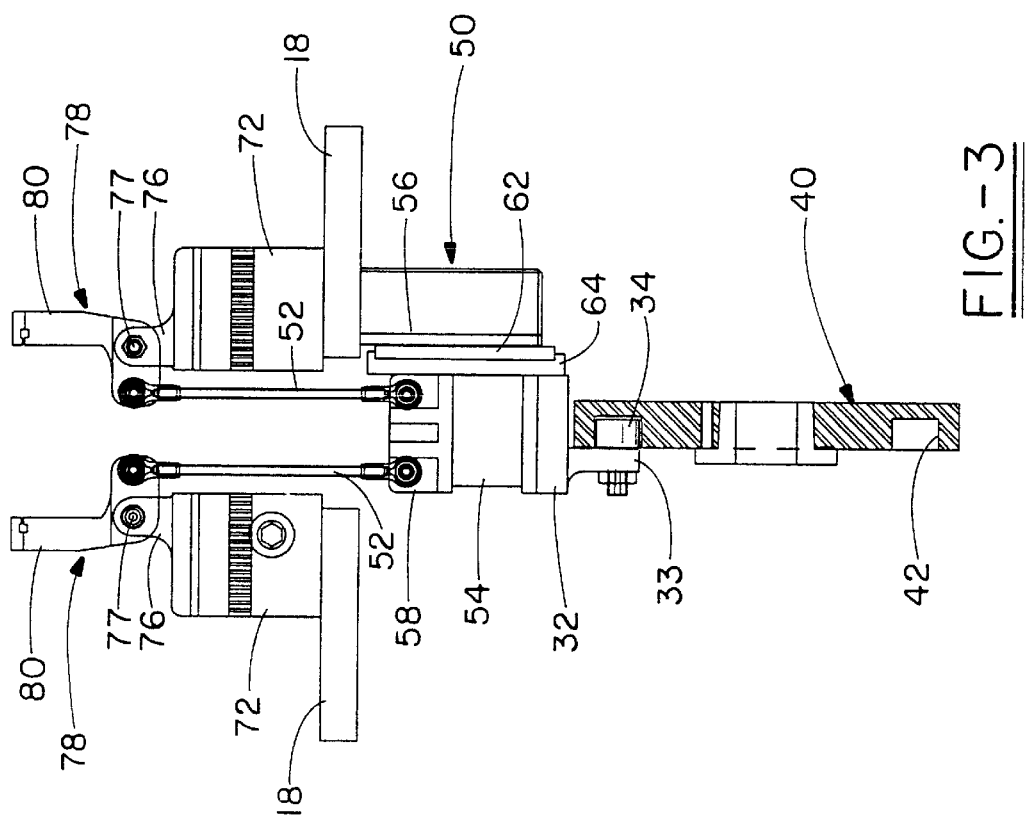
FIG.-3

MULTI-AXIAL STRAIN TESTING APPARATUS

FIELD OF THE INVENTION

The present invention relates to a testing device for materials, and more particularly, to an apparatus which places tensile forces on a sheet, a film, or the like in at least two axes and generally in a radial direction. The testing apparatus can advantageously be employed to test crack propagation and flex fatigue in polymers, elastomers, and rubber.

BACKGROUND OF THE INVENTION

Throughout recent history numerous devices have been developed and constructed to determine or monitor various mechanical properties of almost any material. One such device is a tensometer, which elongates, often repeatedly, a test material in a single axis. The strength, modulus, elongation as well as other characteristics of materials can be obtained from a tensometer.

U.S. Pat. No. 4,535,636 to Blackburn et al. relates to a mechanical extensometer for use with a constant load creep test machine, wherein the dead weight of the extensometer is counterbalanced by two pairs of weights and connected through a pulley system to a rod extension leading into the furnace where a test sample is undergoing elevated temperature tensile testing. Gripper surfaces, a conical tip and a flat surface, are provided in each sample to reduce the grip pressure normally required for attachment of the extensometer to the specimen and reduce initial specimen bending normally associated with foil-gage metal testing.

U.S. Pat. No. 4,248,096 to Marcum relates to a machine for cyclically applying a force to material specimens for testing the fatigue properties thereof. The specimens are positioned between two members, at least one of which moves angularly in a wobble type of action in a cyclic operation. Enclosure members enclose any suitable desired fluid within which the test specimens are tested.

U.S. Pat. No. 4,574,642 to Fleischman relates to an apparatus for monitoring and measuring the growth of a crack in an elastic specimen. The specimen is repeatedly flexed by a piston at a set frequency and periodically slowed to a substantially lower frequency during which time a line scan camera monitors the length of the crack. The camera is positioned such that the specimen is drawn through the scan line thereof. The camera is calibrated such that the output signal from the camera correlates directly to the cracklength. This output signal is digitized, received, and stored by a digital processor for use in determining the crack growth rate.

ASTM test D4482-85 titled "Rubber Property—Extension Cycling Fatigue" describes a test method that uses a machine commonly referred to as the Monsanto "Fatigue to Failure" machine. This machine uses a cam to exert a pre-specified extension onto a rubber specimen at a specific cyclic rate. Once again, the sample undergoes a single axis extension.

ASTM test D813-95, titled "Rubber Deterioration—Crack Growth" describes a test method that uses a machine commonly referred to as a DeMattia Crack Growth tester. A cured sample with a groove at a 90° angle to the specimen length, is cyclically stretched and then compressed, forcing the sample to bend at the groove. The bending motion in the groove stretches the specimen in the low axis direction of the specimen. Again, this exerts a uniaxial stretch in the sample. A small crack or cut can be made in the specimen and the growth of that cut during the test duration is measured.

However, it has been found that the known material testing devices are deficient in being able to simulate natural conditions that polymers, elastomers, and rubber are subject to during actual use. A specific example is a tire sidewall that will experience radial and circumferential strains during its use. Predictions of crack growth in a tire sidewall based on uniaxial testing can be misleading and in some cases cause reversals in the actual performance of different elastomer formulations. Uniaxial and biaxial testing results in different performance levels, see B. J. Roberts and J. B. Benzies, The Relationship Between Uniaxial and Equibiaxial Fatigue in Gum and Carbon Black Filled Vulcanizates, Rubbercon 77, with the biaxial testing being more representative of the actual product performance. The material testing apparatus of the present invention solves the aforementioned problems.

SUMMARY OF THE INVENTION

The present invention relates to a material testing apparatus, which creates a straining or stressing force on a sample in at least two axes and generally in a radial direction. The apparatus of the present invention is able to test numerous materials or samples such as sheets and films of various polymeric compositions, such as rubber tire formulations. The apparatus is also suitable for testing and determining crack growth propagation and flex fatigue of samples. By stressing a sample in at least two axes, an accurate measurement is obtained with respect to a radial direction which substantially mirrors results from those obtained from the ordinary, actual, or intended use of the polymer or rubber.

Other advantages and features of the invention will be apparent from the following description of a preferred embodiment and from the claims.

BRIEF DESCRIPTION OF THE DRAWINGS

The invention will be better understood and other features and advantages will become apparent by reading the detailed description of the invention, taken together with the drawings wherein:

FIG. 3 is a side view of the clamp, transfer, and cam assemblies of the present invention turned 90° in relation to FIG. 2;

FIG. 4 is a side view of the clamp and transfer block assemblies of the multi-axial strain testing apparatus;

FIG. 5 is a top view of the clamping members of the present invention, which are arranged radially about a common centerpoint.

DETAILED DESCRIPTION OF THE INVENTION

Figure 1:
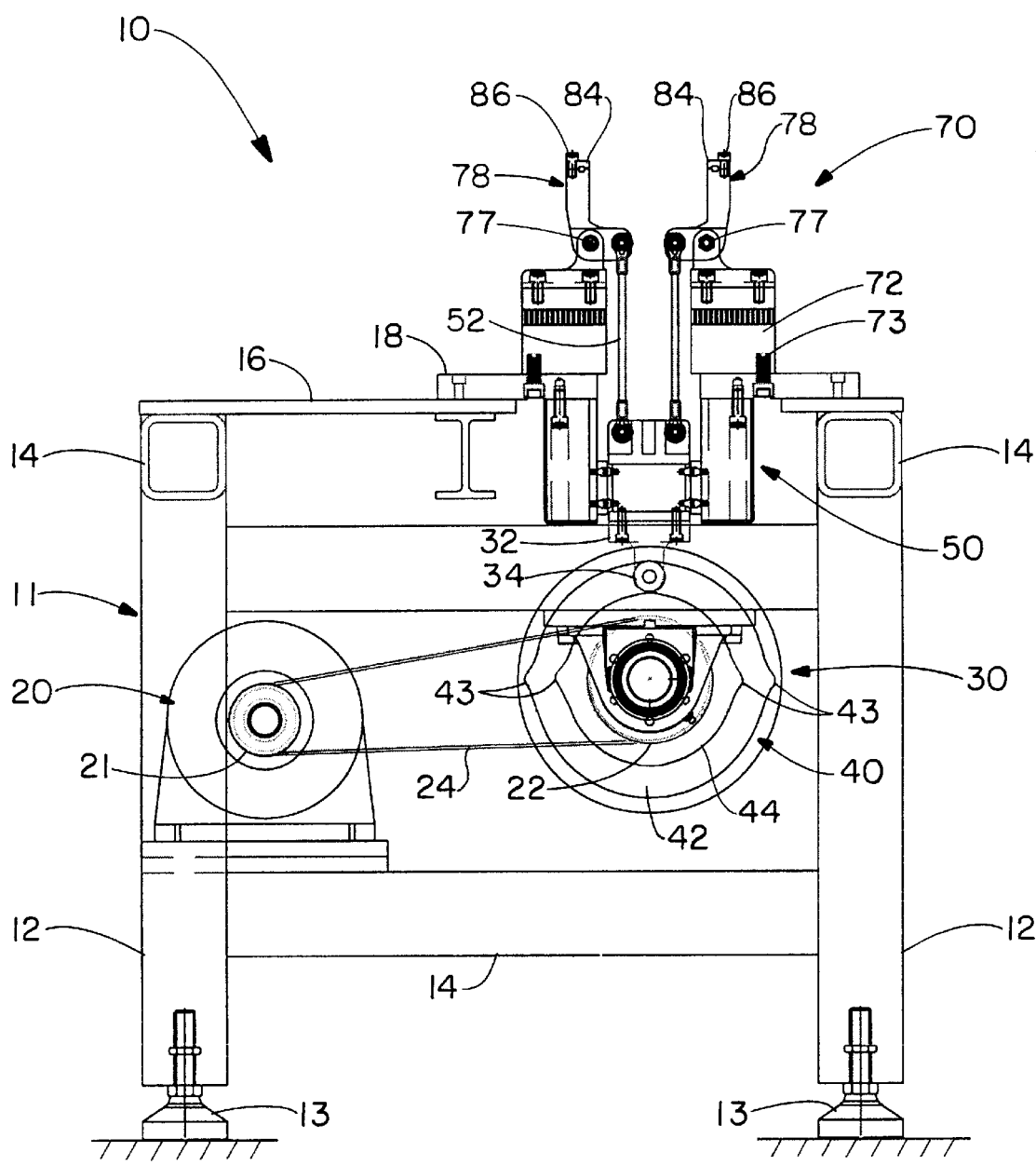
FIG. 1 is a side view of the multi-axial strain testing apparatus having a portion thereof cut away to better illustrate the internal structure.

The multi-axial strain testing apparatus of the present invention is described in detail hereinbelow wherein the preferred embodiment has been set forth. Making reference now to the drawings, the multi-axial strain testing apparatus of the present invention is shown generally in FIG. 1 and is designated by reference numeral 10. The apparatus is supported by frame 11 having legs 12, adjustable supports at least for leveling the apparatus 13, and suitable cross-members 14, upon which a supporting surface 16 can be placed. It is to be understood that frame 11, as shown in FIG. 1, is for mere illustrative purposes and can readily be adapted to other forms or structures which would suitably house or support the apparatus 10. The multi-axial strain testing apparatus 10 further includes a power source 20, a drive assembly such as cam assembly 30, intermediate transfer assembly 50, and clamp assembly 70, all of which will be explained in greater detail hereinbelow.

Figure 2:
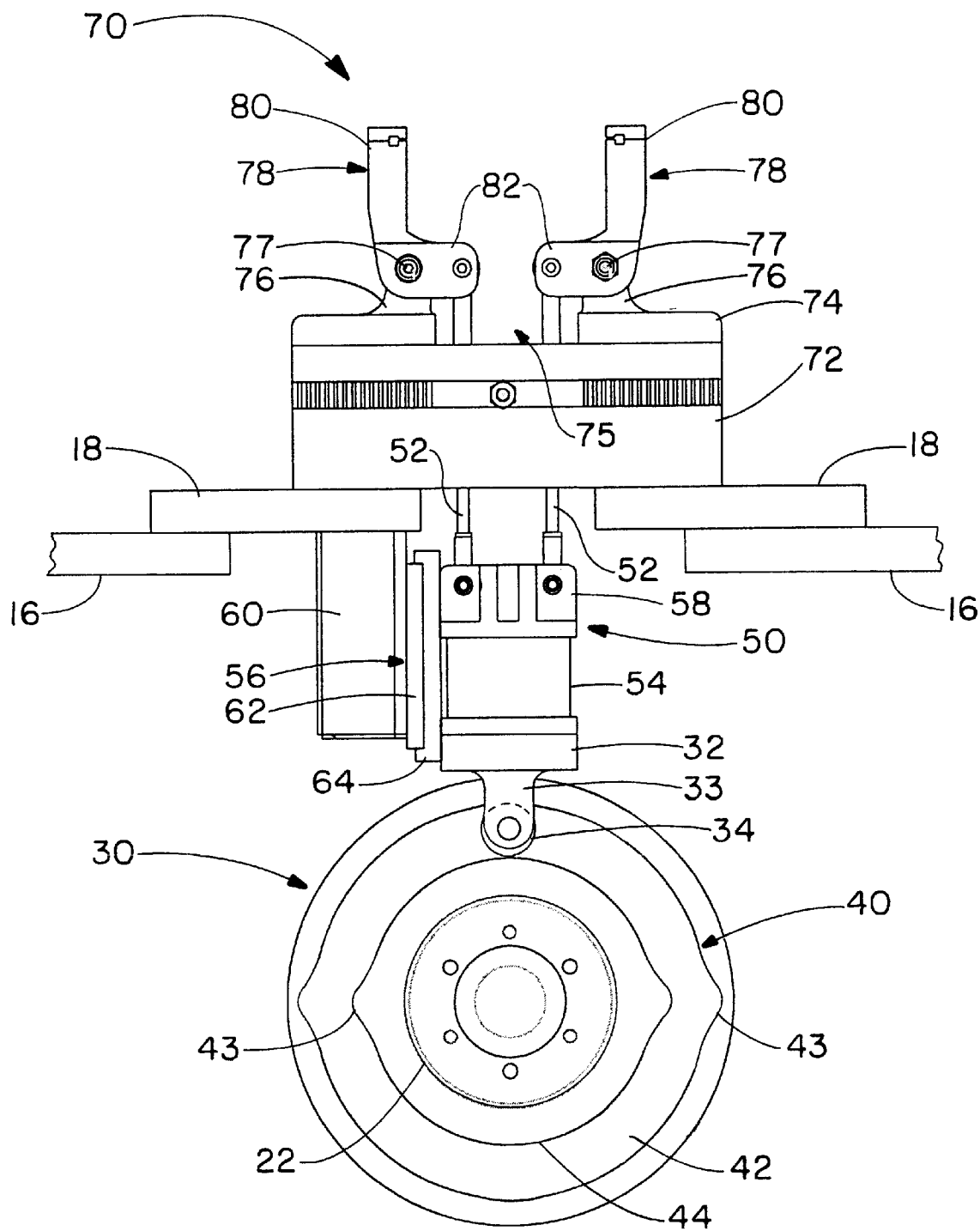
FIG. 2 is an enlarged side view of the clamp, transfer, and cam assemblies wherein the cam is shown having two lobes.

As at least shown in FIG. 2, support plate 18 is connected to supporting surface 16. Plate 18 has clamp base 72 secured thereto such as by threaded screws 73 as shown in FIG. 1, although one skilled in the art will readily realize numerous alternative securing or fastening mechanisms can be utilized such as welding, nuts and bolts, etc. Clamp base 72 is radial in shape as shown in FIG. 1, but can be any shape as long as the base has an aperture or open area 75 in the central portion thereof in order to allow passage for the moving or working elements of the apparatus.

A clamp pivot pedestal 74 is secured to the top, outer portion of base 72. Inasmuch as the testing apparatus is multi-axial, that is, places multi-axial forces on a sample, at least three and preferably four pivot pedestals are utilized and are generally radially arranged on the base so the pedestal head portions 76 are positioned at directions of about 0°, 90°, 180°, and 270° with respect to a centrally located point in open area 75, generally diametrically between the pivot pedestals.

A clamping member 78 is pivotally secured to each pivot pedestal 74 at the head portion thereof as shown in at least FIGS. 2, 3, and 4 through any suitable fastener as stated hereinabove. Clamp 78 is generally L-shaped and includes a sample or material securing element or portion 80 on one side of pivot point 77 and a foot or motion receiving portion 82 on the other. As can be seen in FIG. 5, the sample securing element includes a section which is archial or semi-circular in shape and forms part of a circle, preferably a substantially 90° circumferential segment of a circle when four clamping members are utilized. It is also easily foreseen that when a different number of clamping members are utilized, the size of the segment would be adjusted accordingly. For example, if six clamping members are utilized, each would substantially form a segment of about 60°, and one of eight clamping members would substantially form about a 45° segment of a circle, and so on.

Transfer assembly 50, as best seen in FIG. 2, is operatively connected to clamp assembly 70 and drive or cam assembly 30 and transfers the motion or movement produced by the drive or cam assembly to each of the four clamping members 78. The transfer assembly can be loosely defined as an apparatus for transferring a predetermined motion to the clamp assembly of the present invention to cause cycling or desired movement thereto. The transfer assembly generally comprises transfer rods, a transfer block assembly, bearings and the associated fastening elements therefore.

A transfer rod 52 is operatively fastened to each clamp 78 at the foot portion 82 at one end and operatively fastened to transfer block assembly 54 at the opposite end. Although the transfer rod is shown in the drawings as being substantially linear, any design of transfer rod, i.e. slightly bent, angled, etc., can be utilized so long as the clamping member can be properly pivoted.

Transfer assembly 50 generally includes upper plate 58, main block 54, cam follower mounting block 32, and any suitable bearing such as linear bearing 56. More specifically, an end of a transfer rod is pivotally or moveably connected to the machined upper portion or plate 58 of the transfer block utilizing a suitable fastener element. The upper plate is bolted to main block 54. The main block shown in the drawings is square shaped, but can be of any shape as long as it functions to transfer motion produced by the cam assembly to the clamping assembly.

The bottom or lower end of the main transfer block 54 is connected, preferably bolted, to a cam follower mounting block 32 which is generally "L" shaped. The lower or distal end of the cam follower mounting block 32 has a foot portion 33, which is connected to cam follower 34. The cam follower shown in FIGS. 3 and 4 is a roller bearing mounted on a threaded stud preferably one inch wide and one inch long, although any number of suitably sized roller bearings can be substituted therefore.

The present invention includes a drive assembly such as cam assembly 30. Cam 40, which can be seen in FIGS. 1, 2, and 3, transfers movement through transfer rods 52 and causes cycling of the strain testing apparatus. Cam 40 has a cam follower groove 42 in which cam follower 34 rides. The shape of the cam and groove is such that the rotation of the cam operatively causes the clamping member to pivot and cycle. The cam and cam guide or groove thereof is provided with lobes, such as ridges or high points 43, generally neutral areas 44, and valleys or depressions upon which the cam follower travels. The cam groove has an inner surface located toward the center of the cam and an outer surface upon which the cam follower rides. Generally the inner surface provides an upstroke when the cam follower encounters ridge 43 on the cam groove path. The outer surface thus generally causes a downstroke where a valley or lowering lobe or portion is encountered. The inner and outer surfaces of the guide groove are substantially an equal radial distance from each other throughout the guide groove path or cycle.

The profile or pattern of the cam groove 42 causes the cam follower to reciprocate and move generally in an up and down direction. The movement of the cam follower in turn operatively cycles the clamping members through the above-described connected structure. Lobes and depressions can be inserted anywhere around the circumference of the cam along the path of the cam groove. The shape of the lobes and width of the lobes can also be varied. One preferred orientation places lobes with high rates of up and down motion at widely spaced locations around the cam. This results in a pulse motion being applied to the clamping members.

Although the drive assembly of the present invention is shown as a mechanical mechanism utilizing a rotating cam, a follower, linear bearings, connecting rods and the like to oscillate the clamping fixtures, creating the desired multi-axial motion on the test specimen, alternate drive means can be used to achieve the same result. The mechanical means used provided for rapid prototyping with minimum initial cost allowing concept validation for the test. Alternate means of drive motion include, but are not limited to hydraulic, pneumatic or solenoid actuated drive assemblies. Through computer controls, these alternative means of drive motion increase the variations of test parameters that can be presented to the specimen during testing.

While only one particular cam is shown in FIGS. 1–3, it is to be understood that numerous different cam designs of various patterns can be utilized in order to vary the rate of test sample movement.

Figure 6A:
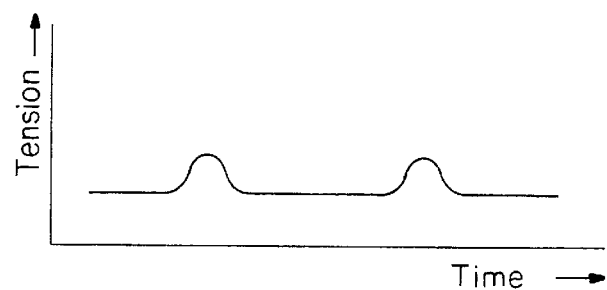
FIGS. 6A–6E show a few variations of possible cycle profiles resulting from utilizing cams having different cam patterns.
Figure 6B:
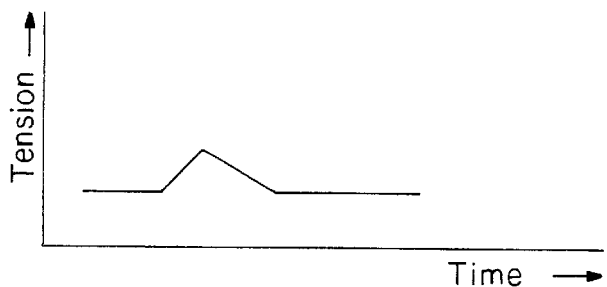
Figure 6C:
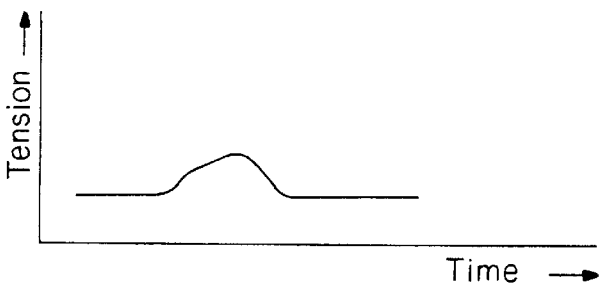
Figure 6D:
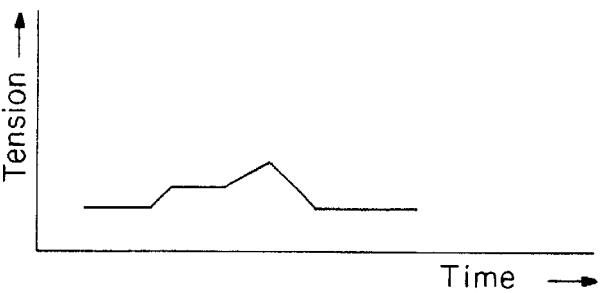
Figure 6E:
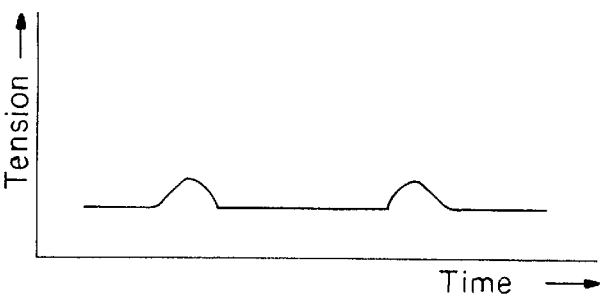

FIG. 6A shows a linear diagram of sample movement utilizing the cam as shown in FIGS. 1–3. The generally horizontal line represents the portion of the guide groove when no tension is placed on the sample. The hump or raised portion is a period of greater tension which is placed on the sample when a lobe or the like is encountered. As shown in FIGS. 6B and 6C, the rate of test sample movement does not have to be linear or symmetrical. Acceleration rates on either side of the ramp can be different simply by providing a cam of varying lobes or valley design. Furthermore, a dwell cycle can be achieved after the test sample is placed under tension, see FIG. 6D. The cam profile can also induce multi-phase or impact loading, as shown in FIG. 6E.

Cam wheel 40 is operatively connected to and driven by a power source 20 such as a one horsepower motor as seen in FIG. 1 through a pulley 22 and belt 24. While numerous variations can exist, the cam of the present invention rotates at 180 RPM on a common 2" diameter jackshaft, supported by a three pillow block bearing. The cam shown in FIGS. 1–3 has two lobes, 180° apart, each with a 0.7056 inch lift. Any other known power transfer source can be utilized to connect cam wheel 40 to a power source such as but not limited to a rod drive or chain drive, etc. Power source 20 is operatively attached to the frame such as on cross-member 14.

As can be seen in FIG. 5, the clamping members 78a, 78b, 78c, and 78d are arranged in a substantially radial manner about a point A. Point A can be considered the (zero, zero) coordinate for an x-y graph or, as previously noted, the radial center of the clamp. Thus, clamping member 78a is located in the positive x direction; clamping member 78b is located in the negative y direction; claming member 78c is located in the negative x direction, and clamping member 78d is located in the positive y direction. As each clamping member has a substantially opposite counterpart, it is easily seen that the strain testing apparatus is bi-axial or multi-axial and imparts a radial tensile force to the sample. By multi-axial, it is meant that radial forces are applied to the sample in a plurality of directions such as 3, 4, 5, 10, etc., or infinite axes due to the radial configuration of the clamping members. In operation, each clamping member cyclically rotates or pivots towards and away from the central midpoint A, consequently straining or stretching a sample held therebetween and subsequently returning the sample to its original position based on cam profile.

The described configuration of clamping points allows a substantially uniform strain to be applied 360° so that at the center of the specimen, there is substantially equibiaxial strain. Points further away from the center can see substantially anisotropic strains because of the clamping configuration. If a small circle is drawn around the center of the sample, when the clamping segments are extended the circle will remain essentially round. A large circle closer to the clamping segments will see a slight flattening of the circle between clamping segments. The flattening is believed to be at least in part because the clamping segments apply a substantially uniform radial strain, but between the clamping segments there is little radial extension, and mostly circumferential strain applied.

Each clamping member 78 includes a sample-restraining portion or chuck 84 to secure the material to be tested by the apparatus. As seen in at least FIGS. 1 and 3, sample-restraining chuck 84 is fastened to sample securing element 80 through a suitable fastening member 86, with the sample material being secured there between. The sample restraining chuck or sample securing element, or both, can be grooved as shown or otherwise modified in order to more securely hold a sample in place.

Samples are prepared by using standard compression molding techniques that are familiar to those skilled in the art. The preferred test samples are a molded six-inch substantially circular disk, substantially 0.070 inches in thickness with a ¼ inch bead around the perimeter. The bead allows clamping of the sample only by the perimeter, in at least three or four distinct quadrants for applying multi-axial strain. The bead around the circumference of the sample fits into the grooves of the clamping segments. The sample can be cured (if thermosetting) or heated and compressed into shape (if thermoplastic) using temperatures, times and procedures common throughout the industry.

The operation of the multi-axial strain testing apparatus of the present invention is as follows. A polymer, rubber, etc., material to be tested is restrained in the clamp assembly and more specifically in the clamping members thereof, between the sample securing element and the sample restraining chuck 84. The samples can be tested with or without initial cracks, cuts, or flaws inserted into the sample. Samples tested without initial flaws would constitute a fatigue to failure test. Samples with an initial flaw would constitute a crack growth test. Initial flaws can be of any desired shape, size or location within the sample. One preferred flaw geometry is a straight cut applied at the center of the sample. The direction of the cut is not specified and can be in any direction related to the grain of the sample or the clamping segments. One preferred orientation is for the cut to be perpendicular to the sample's grain (if any exists) and aimed directly at the center of the clamping segments.

The power source of the multi-axial strain testing apparatus is activated by a suitable switch (not shown) thus causing the power source pulley 21 to activate or rotate belt 24. Belt 24 then acts on pulley 22 causing the cam assembly 30 to rotate through cam 40. As cam 40 rotates, cam follower 34 follows the path of the cam follower groove. The cam follower, through cam follower mounting block 32, acts upon the intermediate transfer assembly specifically, transfer block assembly 54 and transfer rods 52. The intermediate transfer assembly generally slides up and down vertically between linear bearings 56.

Any bearing assembly can be utilized such as linear bearings which are known in the art as linear recalculating ball slides and are designed for low friction linear movement of heavy loads. The bearings include a rail 62 and carriage 64. The rail is used for mounting the bearing to the bearing support block. The carriage slidably rides on the rail and contains ball races. The transfer block assembly is preferably connected to two linear bearing carriages. In turn, the rails of the two bearings are bolted to support blocks 60, 90° in relation to one another. Total sliding movement of the carriages is about 1", although longer or shorter length carriages can also be utilized.

The transfer rods cause clamping member 78 to pivot about clamp pivot point 77. The transfer rods are preferably of equal length, but can be of different lengths if desired to provide a sequential effect to a sample. Clamping members 78 thus are caused to pivot laterally toward and away from a radial central area or mid-point "A" as described hereinabove. The pivoting of the clamping member causes stretching or strain to be applied to the sample material by radially stressing or flexing the same in at least two axial directions.

Any suitable device known to the art and to the literature can be utilized to measure various properties of the sample tested in the strain testing apparatus. Properties such as crack growth, crack development, crack direction (relevant to sample grain), crack shape and crack roughness can suitably be tested utilizing the apparatus of the present invention.

A counter such as a magnetic Hall effect switch (not shown) is used to input the count of cycles to an electronic counter. The counter is set for a desired number of counts, such as 4,000 counts, and at completion, the machine stops and crack growth is then measured. The test is continued until a desired growth, such as 75 mm of growth is attained.

The materials which can be utilized in conjunction with the testing apparatus are numerous. Samples to be tested include generally any polymer, rubber, cellulose material, foils and other suitable materials. Preferably, a sample material to be tested is a sheet or film. Frequency of the test can range from about 0.01 Hertz (cycles per second) to about 100 Hertz, with about 1 to about 10 Hertz being preferred.

Alternatively, the multi-axial strength testing apparatus of the present invention can utilize a clamp assembly with any number of clamping members, such as 2, 3, 6, or 8, etc. In reality, any number of clamping members can be radially arranged around a midpoint, point A. Of course, each clamping member would be connected to a transfer rod and operatively to transfer assembly 50. The clamping members would thus collectively exert a radial force on the sample as described above.

The testing apparatus of the present invention also has the capability to place compressive forces on a test sample. For example, the cam is rotated to a location other than where the clamping members could not be further moved toward the center of the apparatus, i.e. wherein no inward movement towards point A were allowed. A test sample would then be properly secured to the clamping members. Upon cycling, the sample would be both placed under tension and compressed.

EXAMPLES

The following examples serve to illustrate, but not to limit, the present invention.

Three tire sidewall compounds were tested to illustrate the type of results available from this machine. The three compounds had the same formulations and differed only in the amount of sulfur and accelerator present.

The sample compounds were cured in a mold to produce specimens suitable for testing on the described test apparatus. Before testing, a cut was made in the center of each specimen. Length and orientation to the specimen grain is listed with the data. The specimens were clamped into the machine using the outer clamping segments. The grain of the test specimen was always oriented towards the center of one of the clamping segments. The segments were expanded 0.020 inches away from the specimen center in order to apply a small pre strain to the specimen. The cyclic strain was applied in a pulse fashion at 6 Hertz, i.e. 360 stretch cycles per minute. Measurements were recorded until the crack length grew an additional 50 mm.

Example #1, utilizing a 17 mm cut in the center of the specimen at 90° to the specimen grain.

|  | Compound A | Compound B | Compound C |
| --- | --- | --- | --- |
| Crack growth (mm) at | | | |
| 1000 cycles | 1 | 1 | 1 |
| 2000 cycles | 1 | 1 | 2 |
| 6000 cycles | 7 | 2 | 11 |
| 10,000 cycles | 11 | 6 | 15 |
| 14,000 cycles | 13 | 12 | 23 |
| 18,000 cycles | 15 | 13 | 47 |
| 22,000 cycles | 21 | 15 | 67 |
| 26,000 cycles | 29 | 18 | |
| 30,000 cycles | 36 | 19 | |
| 34,000 cycles | 48 | 23 | |
| 38,000 cycles | 61 | 23 | |
| 42,000 cycles | 69 | 26 | |
| 46,000 cycles | | 30 | |
| 50,000 cycles | | 30 | |
| 54,000 cycles | | 31 | |
| 58,000 cycles | | 31 | |
| 62,000 cycles | | 35 | |
| 66,000 cycles | | 38 | |
| 70,000 cycles | | 43 | |
| 74,000 cycles | | 47 | |
| 78,000 cycles | | 52 | |

|  | Compound A | Compound B | Compound C |
| --- | --- | --- | --- |
| Sulfur content (phr) | 1.8 | 1.3 | 1.3 |
| Accelerator* (phr) | 0.75 | 0.75 | 1.25 |
| *N-t-butyl-2-benzothiazyl sulfenamide | | | |
| Physical Properties | | | |
| 300% Modulus (MPa) | 5.33 | 4.62 | 6.45 |
| Tensile (Mpa) | 17.6 | 18.8 | 19.3 |
| Elongation (%) | 660 | 725 | 625 |
| Die C Tear (kgf/cm) | 65.5 | 70.1 | 36 |
| Monsanto Fatigue to Failure per ASTM D4482-85 Cam 14 | | | |
| Average of 6 samples | 699,800 | 352,250 | 572,400 |
| DeMattia Cut Growth per ASTM D813-95 | | | |
| Cut growth (mm) at | | | |
| 1000 cycles | 2 | 2 | 2 |
| 2000 cycles | 2 | 2 | 2 |
| 3000 cycles | 3 | 2 | 3 |
| 5000 cycles | 3 | 2 | 4 |
| 7500 cycles | 5 | 2 | 5 |
| 10,000 cycles | 6 | 2 | 6 |
| 15,000 cycles | 8 | 3 | 7.5 |
| 20,000 cycles | 10 | 3.5 | 10 |
| 25,000 cycles | 12.5 | 4.5 | 12.5 |
| 50,000 cycles | — | 5.5 | — |
| 75,000 cycles | — | 8.9 | — |
| 100,000 cycles | — | 11 | — |

Example #2, utilizing a 17 mm cut in the center of the specimen and parallel to the grain direction of the specimen.

|  | Compound A | Compound B | Compound C |
|---|---|---|---|
| Crack growth (mm) at |  |  |  |
| 1000 cycles | 1 | 1 | 3.5 |
| 4000 cycles | 9 | 5 | 3.5 |
| 8000 cycles | 25 | 14 | >50 |
| 12,000 cycles | 37 | 23 |  |
| 16,000 cycles | 55 | 26 |  |
| 20,000 cycles |  | 52.5 |  |

Example #3, utilizing a 12 mm cut in the center of the specimen at a 45° angle to the grain direction of the specimen

|  | Compound A | Compound B | Compound C |
|---|---|---|---|
| Crack growth (mm) at: |  |  |  |
| 1000 cycles | 0 | 0 | 0 |
| 4000 cycles | 0.5 | 1 | 4 |
| 8000 cycles | 1.5 | 3.5 | >50 |
| 12,000 cycles | 4.5 | 6 |  |
| 16,000 cycles | 7.5 | 8 |  |
| 20,000 cycles | 12.5 | 10 |  |
| 24,000 cycles | 18 | 12 |  |
| 28,000 cycles | 25 | 14 |  |
| 32,000 cycles | 38 | 21 |  |
| 36,000 cycles | 48 | 28 |  |
| 40,000 cycles | 59 | 35 |  |
| 44,000 cycles |  | 42 |  |
| 48,000 cycles |  | 47 |  |
| 52,000 cycles |  | 53 |  |

The data shows that the orientation of the cut with regard to the specimen grain has a large impact on cut growth. Cut growth is slowest when the initial cut is perpendicular to the grain and fastest when the cut is parallel to the specimen grain. The ranking of the three compounds remains the same regardless of the cut orientation.

The multi-axial cut growth machine ranks compounds different than the Monsanto fatigue to failure test. The multi-axial cut growth machine and the DeMattia cut growth machine rank these three compounds in the same order, but the multi-axial cut growth machine shows more discrimination and better separation between the compounds.

While in accordance with the patent statutes the best mode and preferred embodiment have been set forth, the scope of the invention is not limited thereto, but rather by the scope of the attached claims.

What is claimed is:

1. A multi-axial testing apparatus, adapted to apply multi-axial forces to a sample, comprising:
    at least two clamping members for imposing dynamic, substantially radial forces on a sample, each said clamping member comprising a sample securing element which are arranged in a substantially radial manner about a point;
    a transfer rod pivotally connected at one end to said clamping member; and
    a drive assembly adapted to cause cycling of said sample, said drive assembly operatively connected to said transfer rod, wherein when said drive assembly is activated each of said clamping members individually, dynamically reciprocate in a predetermined pattern.

2. A testing apparatus according to claim 1, wherein said testing apparatus includes a transfer block assembly operatively connecting said transfer rod to said drive assembly, wherein transfer block assembly includes a bearing, and wherein said drive assembly is a cam drive assembly including a cam.

3. A testing apparatus according to claim 2, wherein said transfer block assembly includes a cam follower mounting block, and wherein said testing apparatus includes a cam follower operatively connected to said cam follower mounting block, and wherein said cam follower is guided in a cam profile of said cam and operatively causes cycling of said sample.

4. A testing apparatus according to claim 3, wherein said clamping member is connected to a clamp pivot pedestal which is operatively connected to a supporting surface.

5. A testing apparatus according to claim 4, wherein said multi-axial testing apparatus includes four clamping members and a transfer rod operatively connected to each said clamping member, and wherein each said sample securing element which is substantially archial in shape substantially forming a circumferential segment of a circle.

6. A testing apparatus according to claim 5, wherein said transfer block assembly includes an upper plate to which said transfer rods are connected, a main block connected to said upper plate, and wherein said main block is connected to said cam follower mounting block, and wherein said cam drive assembly is driven by a motor.

7. A testing apparatus according to claim 1, wherein said testing apparatus includes four clamping members and four transfer rods, and wherein said sample securing element is substantially in the shape of a 90° arc segment of a circle.

8. A testing apparatus according to claim 7, wherein said clamping member includes a foot portion which is operatively connected to said transfer rod.

9. A testing apparatus according to claim 1, wherein said drive assembly is a cam drive assembly, a pneumatic drive assembly, or a hydraulic drive assembly.

10. A multi-axial testing apparatus, comprising:
    a clamping assembly for placing predetermined dynamic, cyclical tensile forces on a sample in a substantially radial direction, said clamping assembly comprising at least three clamping members, said clamping members each having a sample securing portion for securing a sample to said clamping member, said sample securing portion arranged in a substantially radial manner about a point, wherein each of said clamping members individually, dynamically reciprocate in a predetermined pattern when activated by a drive assembly operatively connected to said clamping assembly through a transfer assembly.

11. A multi-axial testing apparatus according to claim 10, wherein said clamping member includes a motion receiving portion which receive a motion inducing force from said drive assembly operatively connected to said clamping assembly.

12. A multi-axial testing apparatus according to claim 11, wherein said sample securing portion of said clamping member is substantially archial in shape substantially forming a circumferential segment of a circle.

13. A multi-axial testing apparatus according to claim 12, wherein each said clamping member is attached to a transfer rod of said transfer assembly which is operatively connected to said motion causing drive assembly.

14. A multi-axial testing apparatus according to claim 12, wherein said motion causing drive assembly causes said clamping assembly to place predetermined dynamic tensile forces on said sample in a substantially radial direction from a point.

15. A multi-axial testing apparatus according to claim 14, wherein said clamping assembly includes at least four clamping members.

16. A multi-axial testing apparatus according to claim 15, wherein said motion inducing drive assembly is a cam drive assembly, a pneumatic drive assembly, or a hydraulic drive assembly.

17. A multi-axial testing apparatus according to claim 16, wherein said motion inducing drive assembly is said cam drive assembly, and wherein said cam assembly includes a cam having a cam profile adapted to cause cycling of said sample.

18. A multi-axial testing apparatus according to claim 16, wherein said sample securing portion is substantially in the shape of a 90° arc segment of a circle.

19. A multi-axial testing apparatus according to claim 18, wherein said transfer assembly includes a cam follower mounting block, and wherein said cam drive assembly includes a cam follower operatively connected to said cam follower mounting block, and wherein said cam follower is guided in a cam profile of a cam and is adapted to operatively cause strain cycling of said sample.

* * * * *

UNITED STATES PATENT AND TRADEMARK OFFICE
CERTIFICATE OF CORRECTION

| | | |
|---|---|---|
| PATENT NO. | : 6,606,918 B2 | |
| DATED | : August 19, 2003 | |
| INVENTOR(S) | : Gary L. Day, Michael Carroll and Neal G. Sehm | |

It is certified that error appears in the above-identified patent and that said Letters Patent is hereby corrected as shown below:

<u>Title page,</u>
Item [73], Assignee, please replace "Hankock" with -- Hankook --.

Signed and Sealed this

Twenty-first Day of October, 2003

JAMES E. ROGAN
*Director of the United States Patent and Trademark Office*